US009395326B2

(12) United States Patent
Chen et al.

(10) Patent No.: US 9,395,326 B2
(45) Date of Patent: Jul. 19, 2016

(54) FET SENSING CELL AND METHOD OF IMPROVING SENSITIVITY OF THE SAME

(71) Applicant: Taiwan Semiconductor Manufacturing Company Limited, Hsin-Chu (TW)

(72) Inventors: Tung-Tsun Chen, Hsinchu (TW); Jui-Cheng Huang, Hsinchu (TW); Chin-Hua Wen, Toufen Township (TW); Chun-wen Cheng, Zhubei (TW); Yi-Shao Liu, Zhubei (TW)

(73) Assignee: Taiwan Semiconductor Manufacturing Company Limited, Hsin-Chu (TW)

( * ) Notice: Subject to any disclaimer, the term of this patent is extended or adjusted under 35 U.S.C. 154(b) by 153 days.

(21) Appl. No.: 14/069,823

(22) Filed: Nov. 1, 2013

(65) Prior Publication Data

US 2015/0125872 A1 May 7, 2015

(51) Int. Cl.
*G01N 27/414* (2006.01)
*G01N 33/543* (2006.01)

(52) U.S. Cl.
CPC ...... *G01N 27/4145* (2013.01); *G01N 33/54373* (2013.01)

(58) Field of Classification Search
CPC ..................... G01N 27/4145; G01N 33/54373
See application file for complete search history.

(56) References Cited

U.S. PATENT DOCUMENTS 7,049,645 B2 5/2006 Sawada et al.
8,728,844 B1 * 5/2014 Liu .................. H01L 29/66477 257/252
2005/0230271 A1 * 10/2005 Levon ................ G01N 27/4148 205/789
2007/0247170 A1 * 10/2007 Barbaro ............. G01N 27/4145 324/653
2007/0295988 A1 * 12/2007 Yamamoto ......... G01N 27/4145 257/147
2010/0072976 A1 * 3/2010 Sheu .................. G01N 27/4145 324/71.1
2010/0167938 A1 * 7/2010 Su ........................ C12Q 1/6837 506/7
2010/0194409 A1 * 8/2010 Gao ..................... C12Q 1/6825 324/693
2013/0105868 A1 5/2013 Kalnitsky et al.

OTHER PUBLICATIONS

Lee, et al., Ion-Sensitive Field-Effect Transistor for Biological Sensing, Sep. 7, 2009, ISSN 1424-8220, Sensors 2009, 9, pp. 7111-7131; doi:10.3390/s90907111, www.mdpi.com/journal/sensors.
Lee, et al., "A DNA Potentiometic FET Sensor Based on the Direct Charge Accumulation", 15th International Conference on Miniaturized Systems for Chemistry and Life Sciences, Oct. 2-6, 2011, Seattle, Washington, USA, pp. 604-606.

(Continued)

*Primary Examiner* — Melanie Y Brown
(74) *Attorney, Agent, or Firm* — Cooper Legal Group, LLC

(57) ABSTRACT

The present disclosure provides a device, such as a FET sensing cell, which includes a first dielectric layer over a substrate, an active layer over the first dielectric layer, a source region in the active layer, a drain region in the active layer, a channel region in the active layer situated between the source region and the drain region, a sensing film over the channel region, a second dielectric layer over the active layer, wherein an opening is formed in the second dielectric layer and the sensing film is located within the opening, a first electrode located within the second dielectric layer and a fluidic gate region located over the second dielectric layer and extending into the opening. The present disclosure also provides a method for improving the sensitivity of a device by adjusting a sensing value.

20 Claims, 8 Drawing Sheets

200 206 205 215 213 217 216 290 220 210 214 211 204 218 219 203 207 208 209 202 212 201

(56) References Cited

OTHER PUBLICATIONS

"An Integrated ISFET Sensor Array", Kazuo Nakazato, Nov. 4, 2009, Sensors 2009, 9, ISSN 1424-8220, pp. 8831-8851.
"An electronic DNA Sensor Chip using Integrated Capacitive Read-out Circuit", Byunghun Lee, Kang-Ho Lee, Jeong-Oen Lee, Mi-Jin Sohn, Suk-Hwan Choi, Se-Won Wang, Jun-Bo Yoon and Gyu-Hyeong Cho, Aug. 31-Sep. 4, 2010, 32nd Annual International Conference of the IEEE EMSS, Buenos Aires, Argentina, pp. 6547-6550.
"CMOS Capacitive Biosensor with Enhanced Sensitivity for Label-Free DNA Detection", Kang-Ho Lee, Sukhwan Choi, Jeong Oen Lee, Jun-Bo Yoon and Gyu-Hyeong Cho, 2012, IEEE International Solid-Stat4 Circuits Conference, ISSCC 2012, Session 6, Medical, Displays and Imagers, 6.6, 3 pgs.
"Label-Free CMOS Bio Sensor with On-Chip Noise Reductin Scheme for Real-Time Quantitative Monitoring of Biomolecules", Seong-Jin Kim and Euisik Yoon, Jun. 2012, IEEE Transactions on Biomedical Circuits and Systems, vol. 6, No. 3, pp. 189-196.
"Silicon Nanowire field-Effect Transistor-Based Biosensors for Biomedical Diagnosis and Cellular Recording Investigation", Kuan-I-Chen, Bor-Ran Li and Yit-Tsong Chen, Feb. 2011, Nano Today (2011) 6, pp. 131-154.

* cited by examiner

FET SENSING CELL AND METHOD OF IMPROVING SENSITIVITY OF THE SAME

BACKGROUND

Field effect transistor (FET) sensing cells are often used for sensing and detecting at least one of ions, bio-entities or biomolecules. FET sensing cells operate on the basis of at least one of electronic, electrochemical, optical, or mechanical detection principles. FET sensing cells that include transistors are sensors that electrically sense charges, photons, and mechanical properties of ions, bio-entities or biomolecules. The detection is performed by detecting the bio-entities, ions or biomolecules themselves, or through interaction and reaction between specified receptors and bio-entities/biomolecules. Such FET sensing cells are manufactured using semiconductor processes and are applicable to integrated circuits (ICs) and microelectromechanical systems (MEMS).

Ion sensitive field effect transistors (ISFETs) and biologically sensitive field-effect transistors, or bio-organic field-effect transistors (BioFETs) are two types of FET sensing cells that include a transistor for electrically sensing ions, biomolecules or bio-entities.

DESCRIPTION OF THE DRAWINGS

Aspects of the disclosure are understood from the following detailed description when read with the accompanying drawings. It will be appreciated that elements and structures of the drawings are not necessarily drawn to scale. Accordingly, the dimensions of the various features is arbitrarily increased or reduced for clarity of disc.

DETAILED DESCRIPTION

Figure 1:
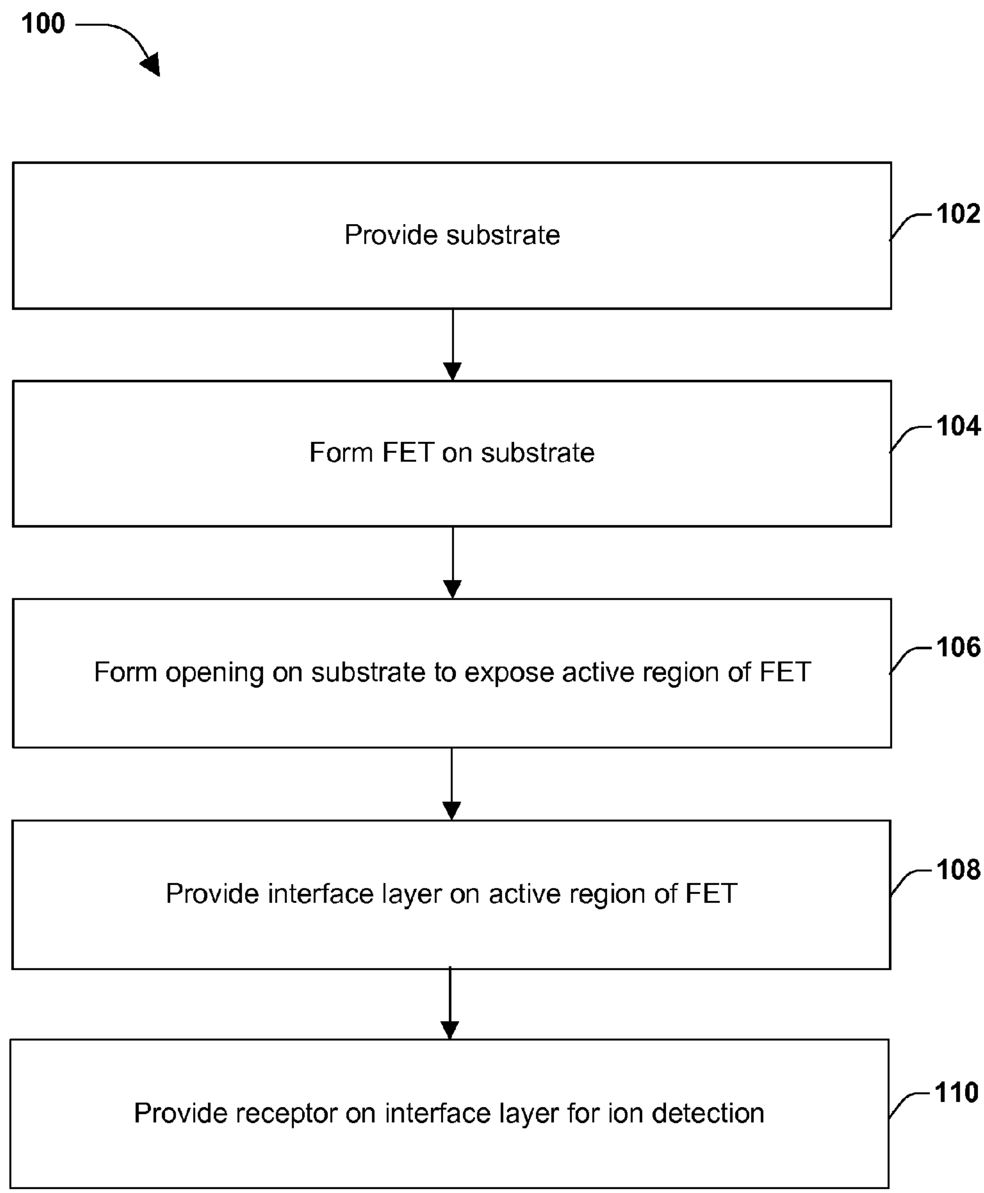
FIG. 1 is a flow diagram of a method for fabricating a device according to some embodiments.

The claimed subject matter is now described with reference to the drawings, wherein like reference numerals are generally used to refer to like elements throughout. In the following description, for purposes of explanation, numerous specific details are set forth in order to provide an understanding of the claimed subject matter. It is evident, however, that the claimed subject matter can be practiced without these specific details. In other instances, structures and devices are illustrated in block diagram form in order to facilitate describing the claimed subject matter.

The present disclosure is directed to, but not otherwise limited to, a device, such as a semiconductor device. In some embodiments, the device is a FET sensing cell. In some embodiments, the device is at least one of an ion sensing field effect transistor (ISFET), a biologically sensitive field effect transistor or bio-organic field effect transistor (BioFET). In some embodiments, the ISFET is a complementary metal-oxide-semiconductor (CMOS) device including a P-type metal-oxide-semiconductor (PMOS) FET device and an N-type metal-oxide-semiconductor (NMOS) FET device. In some embodiments, the device is a BioFET, wherein a gate of a MOSFET (metal-oxide-semiconductor field-effect transistor), which controls the conductance of the semiconductor between its source and drain contacts, is replaced by a bio- or biochemical-compatible layer or a biofunctionalized layer of immobilized probe molecules that act as surface receptors.

In some embodiments, a detection mechanism for ISFETs and BioFETs is a conductance modulation of the transducer due to a binding of a target ion, biomolecule or bio-entity to a gate or a receptor molecule immobilized on the gate. When the target ion, biomolecule or bio-entity is bonded to the gate or the immobilized receptor, the drain current of the FET device is varied by the gate potential. This change in the drain current is measured and the bonding of the receptor and the target ion, biomolecule or bio-entity is identified. A great variety of ions, biomolecules and bio-entities are used to functionalize the gate of the ISFET or BioFET such as ions, enzymes, antibodies, ligands, receptors, peptides, oligonucleotides, cells of organs, organisms and pieces of tissue. In some embodiments, to detect single-stranded deoxyribonucleic acid (ssDNA), the gate of the BioFET is functionalized with immobilized complementary ssDNA strands. Likewise, various proteins such as tumor markers are detected by functionalizing the gate of FET device with monoclonal antibodies.

Illustrated in FIG. 1 is of a method 100 of fabricating a device according to some embodiments. The method 100, in some embodiments, includes forming a FET sensing cell, such as an ISFET, using one or more process acts compatible with or typical to a complementary metal-oxide-semiconductor (CMOS) process.

At 102 a substrate is provided. In some embodiments, the substrate includes a wafer. In some embodiments, the substrate is a silicon substrate. In some embodiments, the substrate includes another elementary semiconductor, such as germanium; a compound semiconductor including at least one of silicon carbide, gallium arsenic, gallium phosphide, indium phosphide, indium arsenide, or indium antimonide; an alloy semiconductor including at least one of SiGe, GaAsP, AlInAs, AlGaAs, GaInAs, GaInP, or GaInAsP; or combinations thereof. In some embodiments, the substrate is a semiconductor on insulator (SOI) substrate. In some embodiments, the substrate includes a buried oxide (BOX) layer formed by a process such as separation by implanted oxygen (SIMOX), oxidation, deposition, or other suitable processes. In some embodiments, the substrate includes doped regions, such as at least one of one or more p-wells or one or more n-wells. In some embodiments, the substrate includes various doped regions depending on design requirements. In some embodiments, the doped regions are doped with p-type dopants, such as boron or BF2; n-type dopants, such as phosphorus or arsenic; or combinations thereof. In some embodiments, the doped regions are formed directly on the substrate, in a P-well structure, in an N-well structure, in a dual-well structure, or using a raised structure.

At 104 a field effect transistor (FET) is formed on the substrate. In some embodiments, the FET includes a fluidic gate region, a source region, a drain region, and a channel region interposing the source and drain regions. In some embodiments, at least one of the source, drain, or channel regions are formed on an active region of the semiconductor substrate. In some embodiments, a first dielectric layer is formed on top of the substrate, an active layer is formed on top of the first dielectric layer and a second dielectric layer is formed on top of the active layer. In some embodiments, the FET is an n-type FET (nFET) or a p-type FET (pFET). In some embodiments, the source/drain regions include n-type dopants or p-type dopants depending on the FET configuration. In some embodiments, the gate structure includes at least one of a gate dielectric layer, a gate electrode layer, or other suitable layers. In some embodiments, the gate structure is a fluidic gate with an electrode in contact with the gate fluid. In some embodiments, the electrode is located about 0.5 microns from the sensing film. In some embodiments, the electrode is aluminum. In some embodiments, the electrodes include metal electrodes including material such as, Cu, W, Ti, Ta, Cr, Pt, Ag, Au; suitable metallic compounds such as TiN, TaN, NiSi, CoSi; combinations thereof; or other suitable conductive materials. In some embodiments two electrodes are present. In some embodiments, an opening is etched into the second dielectric layer for the electrode to be positioned therein. In some embodiments, at least one of the first dielectric layer or the second dielectric layer is silicon oxide. In some embodiments, the gate dielectrics include at least one of silicon nitride, silicon oxynitride, a dielectric with a high dielectric constant (high k), or combinations thereof. In some embodiments, the high k material include hafnium silicate, hafnium oxide, zirconium oxide, aluminum oxide, tantalum pentoxide, hafnium dioxide-alumina ($HfO_2$—$Al_2O_3$) alloy, or combinations thereof. In some embodiments, the FET is formed using CMOS processes.

At 106 an opening is formed on the substrate. In some embodiments, the opening includes a trench formed in one or more layers disposed on the substrate that includes the FET device. In some embodiments, the opening exposes a region underlying the gate and second dielectric layer. In some embodiments, the opening exposes an active region, such as a silicon active region, underlying the gate and active/channel region of the FET device. In some embodiments, the opening is formed using suitable photolithography processes to provide a pattern on the substrate and etching process to remove materials until the body structure of the FET device is exposed. In some embodiments, the etching processes include at least one of wet etch, dry etch, plasma etch or other suitable processes. In some embodiment, a third dielectric layer is formed above the fluidic gate region.

At 108 a sensing film is formed in the opening. In some embodiments, the sensing film is formed on the exposed active region underlying the gate structure of the FET. In some embodiments, the sensing film is compatible for ion, biomolecule or bio-entity binding. In some embodiments, a sensing film is provided as a binding interface for ssDNA. In some embodiments, a sensing film is provided as a binding interface for hydrogen ions. In some embodiments, the sensing film is at least one of a dielectric material, a conductive material, or other suitable material for holding a receptor. In some embodiments, the sensing film materials include high-k dielectric films, metals, metal oxides, dielectrics, or other suitable materials, alone or in combination. In some embodiments, the sensing materials include at least one of $HfO_2$, $Ta_2O_5$, Pt, Au, W, Ti, Al, Cu, oxides of such metals, $SiO_2$, $Si_3N_4$, $Al_2O_3$, $TiO_2$, TiN, SnO, $SnO_2$; or other suitable materials, alone or in combination.

At 110 a receptor such as at least one of an enzyme, antibody, ligand, peptide, nucleotide, cell of an organ, organism or piece of tissue is placed on an sensing film for detection of a target biomolecule. In some embodiments, the receptor is an immobilized complementary ssDNA strand.

Figure 2:
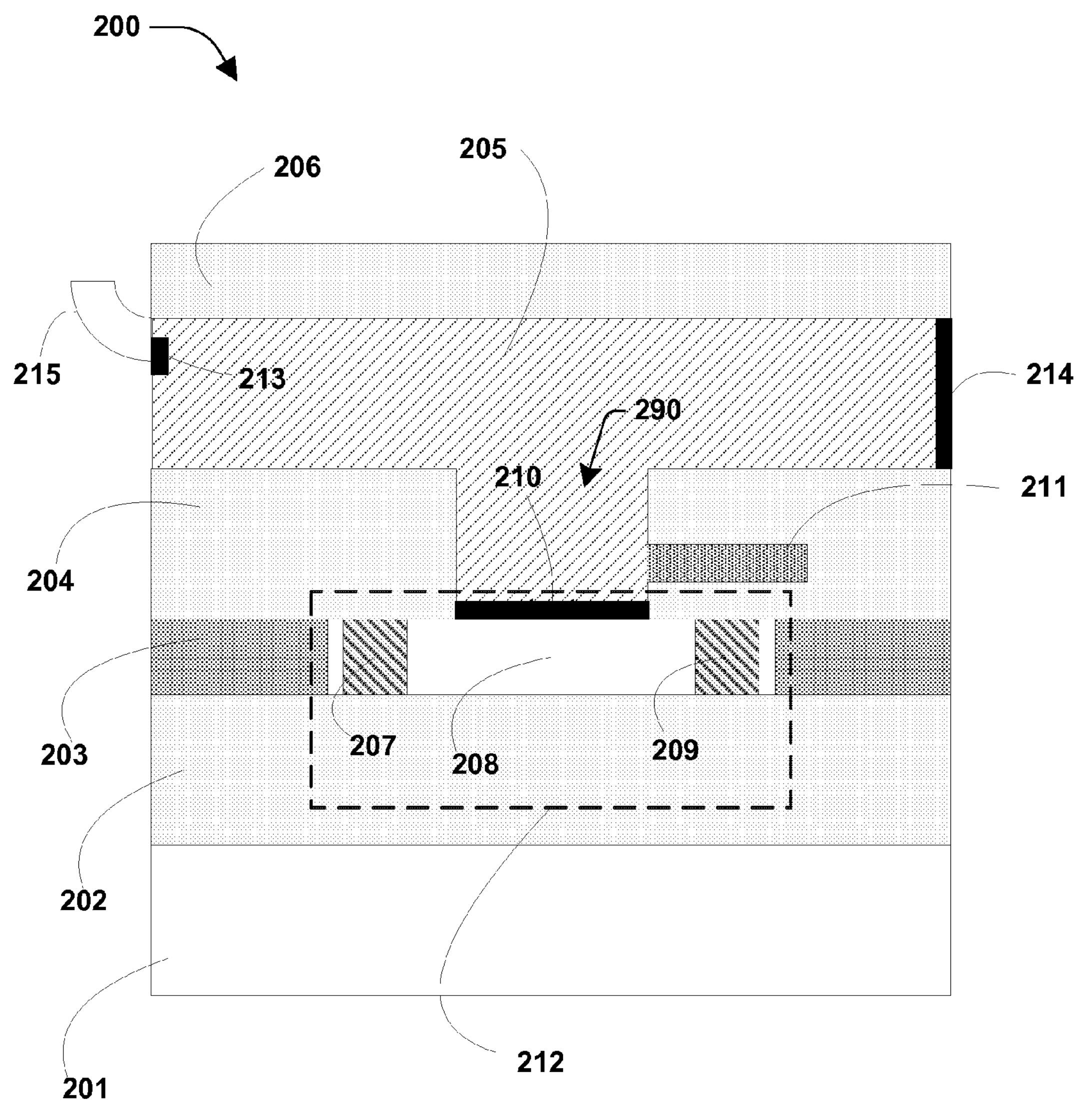
FIGS. 2 to 5 are cross-sectional views of a device according to some embodiments.

Referring now to FIG. 2, illustrated is a device 200 according to some embodiments. In some embodiments, the device 200 includes a FET sensing cell. In some embodiments, the device 200 includes an ISFET or a BioFET. In some embodiments, the device 200 is formed using one or more aspects of the method 100, described above with reference to FIG. 1.

In some embodiments, the device 200 is formed over or upon a substrate 201, and thus includes at least a portion of a substrate in some embodiments. In some embodiments, a first dielectric layer 202 is formed on the substrate 201. In some embodiments, an active layer 203 is formed on the first dielectric layer 202. In some embodiments, the active layer 203 includes a source region 209, a drain region 207, and a channel region 208, interposing the source region 209 and the drain region 207. In some embodiments, a sensing film 210 is located over the channel region 208. In some embodiments, a second dielectric layer 204 is located over the active layer 203. In some embodiments, an opening 290 is defined within the second dielectric layer 204 wherein the sensing film 210 is inserted above the active layer 203. In some embodiments, the sensing film 210 is about 5 nm to about 20 nm thick. In some embodiments, a fluidic gate region 205 is located above the second dielectric layer 203 and extends into the opening 290 above the sensing film 210. In some embodiments, the fluidic gate region 205 is filled with a fluid. In some embodiments, the fluidic gate region 205 is at least partially empty or not filled with a fluid. In some embodiments at least some of the fluidic gate region 205 is filled with air. In some embodiments, an electrode 211 is present in the second dielectric layer 204. In some embodiments, the electrode 211 is positioned as to be in contact with the fluidic gate region 205 in the opening 290. In some embodiments, the electrode 211 is separated from the fluidic gate region in the opening 290 by a dielectric material. In some embodiments, the electrode 211 is about 100 nm to about 300 nm thick. In some embodiments, a first inlet 215 and a first valve 213 are located on one side of the fluidic gate region 205 and an outlet 214 is located on the opposing side of the fluidic gate region 205. In some embodiments, a third dielectric layer 206 is located above the fluidic gate region 205. In some embodiments, the fluidic gate region 205, the source region 209, the drain region 207, first dielectric layer 202, second dielectric layer 204 and the active region 203 are formed using CMOS process technology. In some embodiments, the fluidic gate region 205, source region 209, drain region 207, sensing film 210 and active region 203 form a FET 212.

In some embodiments, the substrate 201 is about 80 microns to about 100 microns thick. In some embodiments, at least one of the first dielectric layer 202 or the second dielectric layer 203 are about 0.5 micron to about 1.5 microns thick. In some embodiments, the active region 203 is about 200 angstroms to about 400 angstroms thick. In some embodiments, the sensing film 210 is about 80 nanometers to about 100 nanometers thick. In some embodiments, a distance from the source region 209 to the drain region 207, or a length of the channel region 208, is about 0.2 microns to about 1 micron.

In some embodiments, the device 200 includes electrical contacts to at least one of the source region 209, the drain region 207, the sensing film 210, or the active layer 203.

In some embodiments, the device 200 includes at least one of additional passive components such as resistors, capacitors, inductors, fuses, or active components, such as at least one of P-channel field effect transistors (PFETs), N-channel field effect transistors (NFETs), metal-oxide-semiconductor field effect transistors (MOSFETs), complementary metal-oxide-semiconductor (CMOS) transistors, high voltage transistors, or high frequency transistors.

Figure 3:
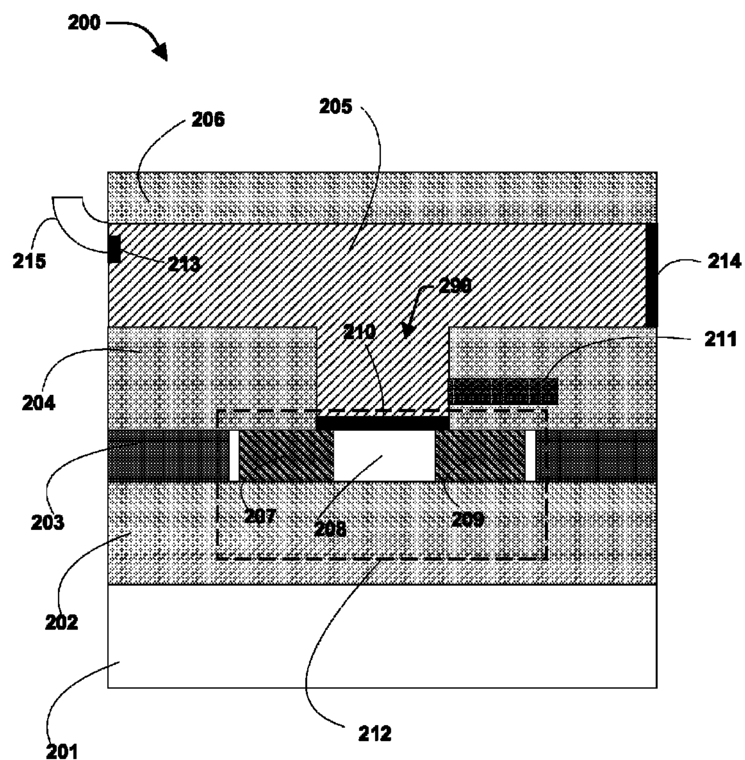

Referring to FIG. 3, the device 200 is illustrated according to some embodiments. In some embodiments, the device 200 includes a FET sensing cell. In some embodiments, the device 200 includes an ISFET or a BioFET. In some embodiments, the source region 209 at least partially extends under the sensing film 210. In some embodiments, the drain region 207 at least partially extends under the sensing film 210.

Figure 4:
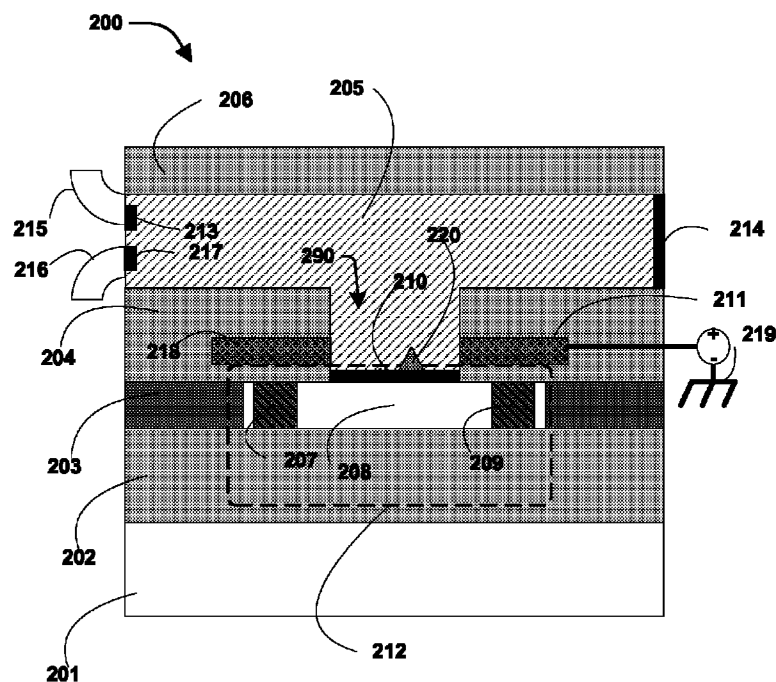

Referring to FIG. 4, the device 200 is illustrated according to some embodiments. In some embodiments, the device 200 includes a FET sensing cell. In some embodiments, the device 200 includes an ISFET or a BioFET. In some embodiments, the device 200 includes a second inlet 216 and a second valve 217 connected to the fluidic gate region 205. In some embodiments, the device 200 includes a second electrode 218 in the second dielectric layer 204. In some embodiments, at least one of electrode 218 or electrode 211 are attached to a voltage source 219 for applying a bias or reference voltage. In some embodiments, electrodes 218 and 211 are used to apply a mono or dielectrophoresis force to control ion movement in a reaction solution. In some embodiments, at least one of the electrodes 218 or 211 are located in the second dielectric layer 204 within about 500 angstroms to about 7500 angstroms of the sensing film 210. In some embodiments, the relatively close proximity of the electrodes 218 and 211 to the sensing film 210 allows for shorter sensing and reset phases, which in turn improves the signal to noise ratio and sensitivity of the device 200. In some embodiments, a receptor 220 is placed on or proximate the sensing film 210 for detection of a target molecule. In some embodiments, the receptor 220 includes at least one of enzymes, antibodies, ligands, peptides, nucleotides, cells of an organs, organisms or pieces of tissue.

Figure 5:
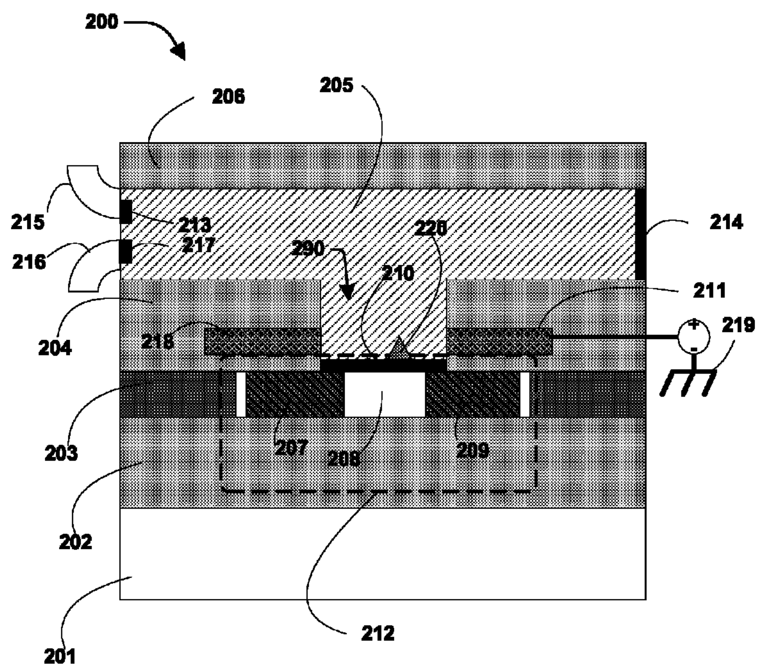

Referring now to FIG. 5, the device 200 is illustrated according to some embodiments. In some embodiments, the device 200 includes a FET sensing cell. In some embodiments, the device 200 includes an ISFET or a BioFET. In some embodiments, the some region 209 at least partially extends under the sensing film 210. In some embodiments, the drain region 207 at least partially extends under the sensing film 210.

Figure 6:
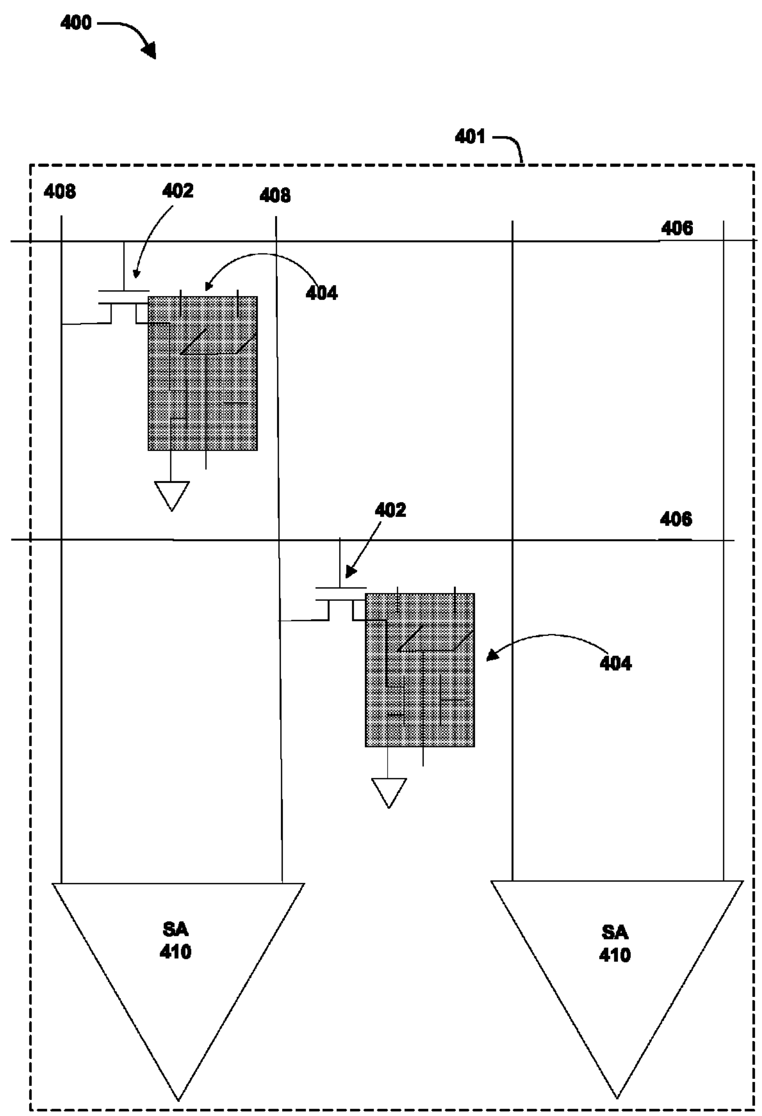
FIG. 6 is a circuit diagram of a plurality of devices configured in an array arrangement according to some embodiments.

Referring now to FIG. 6, illustrated is a schematic of a layout 400 of a plurality of semiconductors 402 and devices 404 connected to lines 406 and lines 408. In some embodiments, the devices are FET sensing cells. In some embodiments, the lines 406 are bit lines. In some embodiments, the lines 408 are word lines. In some embodiments, layout 400 is within a device 401.

In some embodiments, the device 404 includes a BioFET or ISFET. In some embodiments, the semiconductor 402 includes transistors, such as control transistors or switching elements, operable to provide connection to the devices 404.

In some embodiments, the layout 400 includes an array formation that is useful in detecting small signal changes provided by minimal ions, biomolecules or bio-entities introduced to a device 404. In some embodiments, the layout 400 includes sense amplifiers 410. In some embodiments, the sense amplifiers 410 enhance the signal quality and magnification to improve the detection ability of a device having the layout 400. In some embodiments, when particular lines 406 and lines 408 are turned on, the corresponding semiconductors 402 will be turned on, thus allowing the corresponding semiconductor devices 402 to function in an ON-state. In some embodiments, when the gate of an associated device 404 is triggered by the presence of at least one of an ion, bio-molecule or bio-entity, the device 404 will transfer electrons and induce field effect charging of the device, thereby modulating a current, such as Ids. In some embodiments, the change of the current or threshold voltage, such as Vt, serves to indicate detection of at least one of relevant ions, biomolecules or bio-entities. Thus, in some embodiments, a device having the layout 400 achieves a FET sensor cell application including application with differential sensing for enhanced sensitivity.

Figure 7:
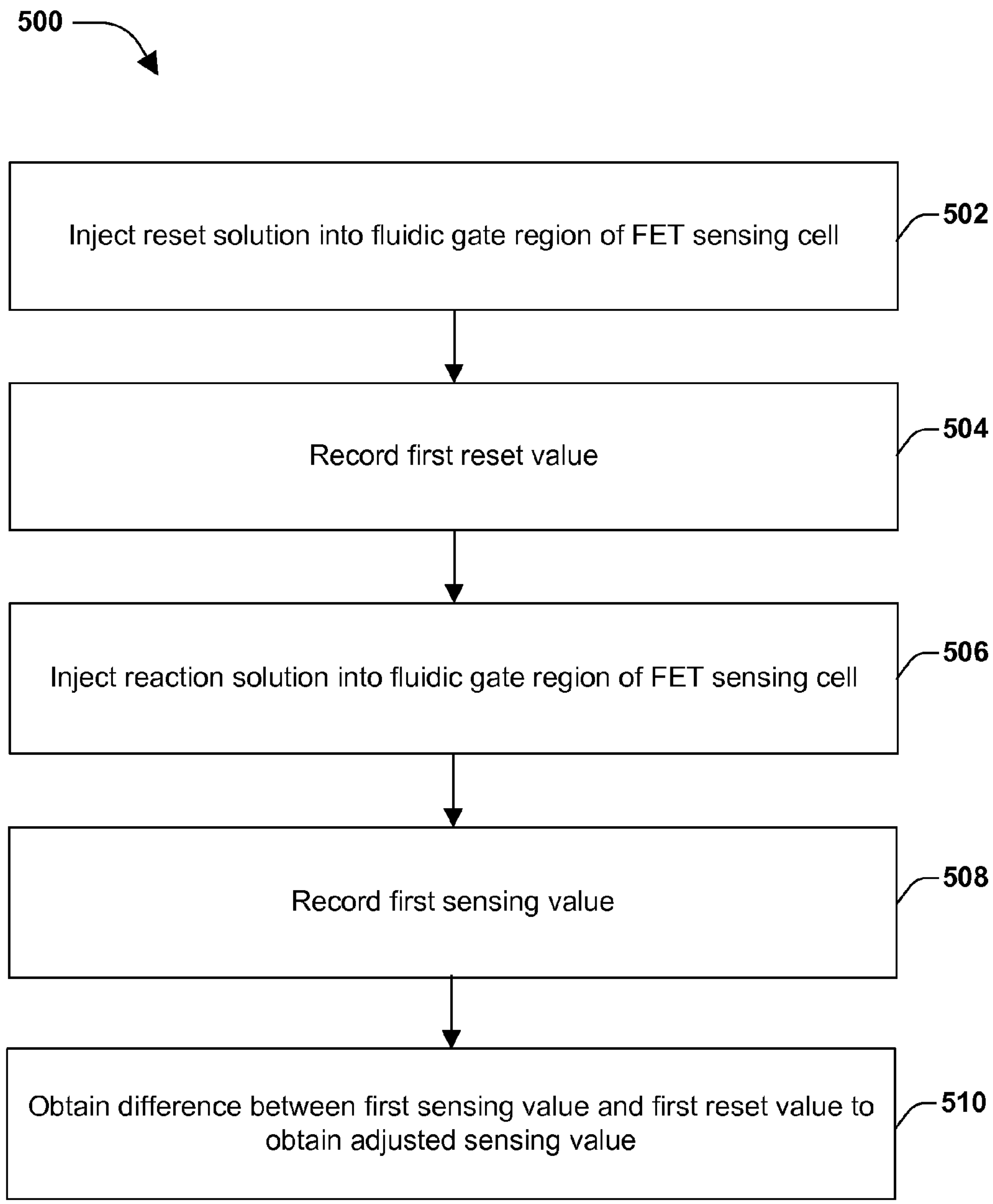
FIG. 7 is a flow diagram of a method for improving sensitivity of a device according to some embodiments.

Referring to FIG. 7, a method 500 for improving sensitivity of a device 200 is provided. In some embodiments, the device 200 is a FET sensing cell. At 502 a reset solution is injected into the fluidic gate region 205 of the device 200. In some embodiments, the reset solution is injected by opening the second valve 217 of the second inlet 216 to inject a first reset solution into the fluidic gate region 205 of device 200. In some embodiments, the reset solution is a buffer solution having a pH from about 1 to about 10. In some embodiments, the reset solution includes a pH buffer solution having a pH from about 7 to about 9.

At 504 a first reset value is recorded from the reset solution interacting with the sensing film 210. In some embodiments, a receptor is on or proximate a surface of the sensing film 210. In some embodiments, the second valve 217 of the second inlet 216 is closed once a stable reading is collected. In some embodiments, the second valve 217 is closed after about 10 microseconds to about 15 microseconds. In some embodiments, a bias is applied by at least one of electrodes 211 or 218 while the first reset value is recorded.

At 506 a first reaction solution is injected into the fluidic gate region 205 of the device 200. In some embodiments, the reaction solution is injected by opening a first valve 213 connected to the first inlet 215. In some embodiments, the reaction solution is a bio-reaction solution. In some embodiments, the reaction solution contains ssDNA. In some embodiments, the reaction solution includes various proteins such as tumor markers or antibodies.

At 508 a first sensing value is recorded. In some embodiments, the sensing film 210 has one or more receptors 220 disposed thereon. In some embodiments, the receptors 220 affect the conductance of the FET 212. If the receptors 220 attach to a molecule provided on the sensing film 210, the resistance of the channel region 208 in the active layer 203 between the source region 209 and the drain region 207 is altered. In some embodiments, the FET 212 is used to detect one or more specific molecule, such as ions, biomolecules or bio-entities. In some embodiments, the device 200 is arranged in an array type pattern such as described above with reference to FIG. 6. In some embodiments, a bias is applied by at least one of electrodes 211 or 218 while the first sensing value is recorded.

At 510 an adjusted sensing value is obtained. In some embodiments, the difference between the first sensing value and the reset value is used to determine the first adjusted value. In some embodiments, the adjusted value is used to remove or at least reduce noise associated with an FET device.

In some embodiments, method 500 is repeated with a second reset solution and a second reaction solution, and a third and a fourth, etc.

In some embodiments, at least one of the electrodes 218 or 211 apply the same voltage while the first reset value and first sensing value are recorded.

Figure 8:
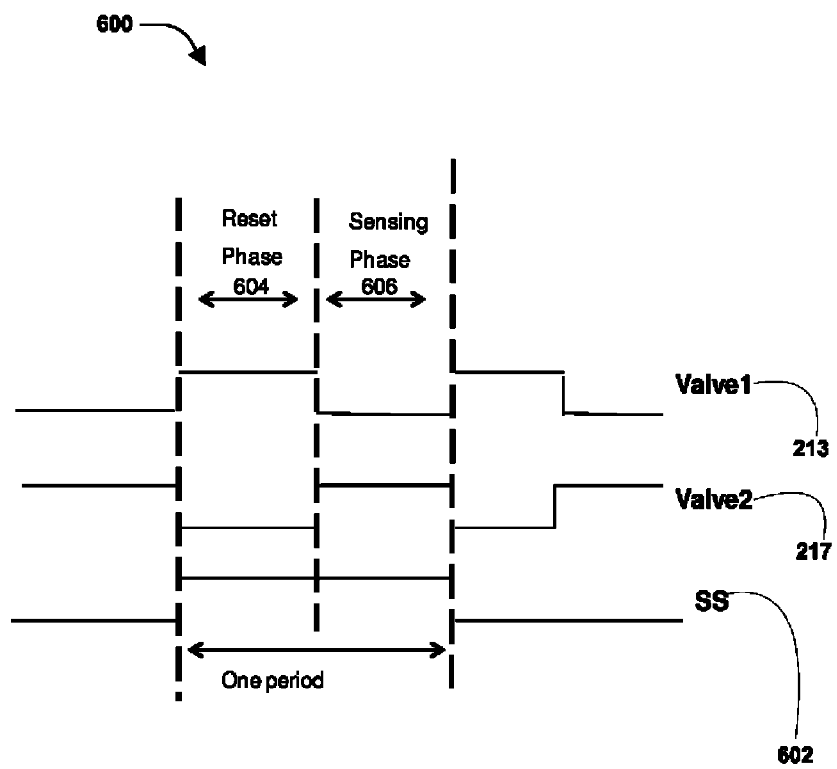
FIG. 8 is an illustration of signal timing for a sensing period according to some embodiments.

Referring now to FIG. 8, a schematic of a layout 600 of a period including a sensing phase and a reset phase is illustrated. In some embodiments, the period corresponds to a method for improving sensitivity such as described above with reference to FIGS. 2, 3, 4, 5 and 7. In some embodiments, the first valve 213 is open and the second valve 217 is closed during the reset phase 604 then the first valve 213 is closed and the second valve 217 is open during the sensing phase 606. In some embodiments, a sensing switch 602 is closed during both the reset phase 604 and the sensing phase 606, where the sensing switch is a switch that, when closed, allows both the first sensing value and the first reset value to be obtained or recorded. In some embodiments, the period is about 5 microseconds to about 50 microseconds. In some embodiments, the first reset value for the reset phase 604 and the first sensing value for the sensing phase 606 are used to determine an adjusted sensing value. In some embodiments, a voltage is sensed when obtaining or recording at least one of the first reset value or the first sensing value. In some embodiments, a current is sensed when obtaining or recording at least one of the first reset value or the first sensing value. In some embodiments, the output of the sensing cell is amplified.

In some embodiments, the device 200 undergoes further CMOS or MOS technology processing to form various features and regions. According to some embodiments, subsequent processing forms various contacts/vias/lines and multilayer interconnect features, such as metal layers and interlayer dielectrics, configured to connect various features or structures of the device 200. In some embodiments, a multilayer interconnection includes vertical interconnects, such as vias or contacts, and horizontal interconnects, such as metal lines. In some embodiments, the various interconnection features implement various conductive materials including copper, tungsten, or silicide, alone or in combination. In some embodiments, at least one of a damascene or dual damascene process is used to form a copper related multilayer interconnection structure.

According to some embodiments, a device includes a first dielectric layer over a substrate, an active layer over the first dielectric layer, a source region in the active layer a drain region in the active layer, a channel region in the active layer situated between the source region and the drain region, a sensing film over the channel region, a second dielectric layer over the active layer, an electrode located within the second dielectric layer; and a fluidic gate region located over the second dielectric layer and the sensing film.

According to some embodiments, a device includes a first dielectric layer over a substrate, an active layer over the first dielectric layer, a source region in the active layer, a drain region in the active layer, a channel region in the active layer situated between the source region and the drain region, a sensing film over the channel region, a second dielectric layer over the active layer, wherein an opening is formed in the second dielectric layer and the sensing film is located within the opening, a first electrode located within the second dielectric layer and a fluidic gate region located over the second dielectric layer and extending into the opening.

According to some embodiments, a method for improving sensitivity of a device by adjusting a sensing value of the device, includes injecting a first reset solution into a fluidic gate region of the device, recording a first reset value based upon the first reset solution interacting with a sensing film of the device, injecting a first reaction solution into the fluidic gate region of the device, recording a first sensing value based upon the first reaction solution interacting with the sensing film of the device and obtaining a difference between the first sensing value and the first reset value to obtain a first adjusted sensing value.

Although the subject matter has been described in language specific to structural features or methodological acts, it is to be understood that the subject matter of the appended claims is not necessarily limited to the specific features or acts described above. Rather, the specific features and acts described above are disclosed as example forms of implementing at least some of the claims.

Various operations of embodiments are provided herein. The order in which some or all of the operations are described should not be construed as to imply that these operations are necessarily order dependent. Alternative ordering will be appreciated given the benefit of this description. Further, it will be understood that not all operations are necessarily present in each embodiment provided herein. Also, it will be understood that not all operations are necessary in some embodiments.

Further, unless specified otherwise, "first," "second," or the like are not intended to imply a temporal aspect, a spatial aspect, an ordering, etc. Rather, such terms are merely used as identifiers, names, etc. for features, elements, items, etc. For example, a first channel and a second channel generally correspond to channel A and channel B or two different or two identical channels or the same channel.

It will be appreciated that layers, features, elements, etc. depicted herein are illustrated with particular dimensions relative to one another, such as structural dimensions or orientations, for purposes of simplicity and ease of understanding and that actual dimensions of the same differ substantially from that illustrated herein, in some embodiments. Additionally, a variety of techniques exist for forming the layers, regions, features, elements, etc. mentioned herein, such as implanting techniques, doping techniques, spin-on techniques, sputtering techniques, growth techniques, such as thermal growth or deposition techniques such as chemical vapor deposition (CVD), for example.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B or the like generally means A or B or both A and B. Furthermore, to the extent that "includes", "having", "has", "with", or variants thereof are used in either the detailed description or the claims, such terms are intended to be inclusive in a manner similar to the term "comprising".

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A device, comprising:

a first dielectric layer over a substrate;

an active layer over the first dielectric layer;

a source region in the active layer;

a drain region in the active layer;

a channel region in the active layer situated between the source region and the drain region;

a sensing film over the channel region;

a second dielectric layer over the active layer;

an electrode located within the second dielectric layer; and a fluidic gate region located over the second dielectric layer and the sensing film, wherein the fluidic gate region is a cavity, the electrode defines a portion of a sidewall of the cavity, and the sensing film defines a portion of a bottom of the cavity.

2. The device of claim 1, comprising:

a third dielectric layer over the fluidic gate region.

3. The device of claim 1, comprising:

one or more inlets connected to the fluidic gate region.

4. The device of claim 1, wherein the electrode comprises at least one of Cu, W, Ti, Ta, Cr, Pt, Ag, Au, TiN, TaN, NiSi, or CoSi.

5. The device of claim 1, wherein the sensing film comprises at least one of $SiO_2$, $Si_3N_4$, $Al_2O_3$, $TiO_2$, $HfO_2$, $Ta_2O_5$, TiN, SnO, $SnO_2$, Pt, Cr, Au, Al, W, or Cu.

6. The device of claim 1, comprising:

a receptor disposed on the sensing film.

7. The device of claim 6, wherein the receptor comprises at least one of enzymes, antibodies, ligands, peptides, nucleotides, cells of organs, organisms or pieces of tissue.

8. A device, comprising:

a first dielectric layer;

an active layer over and in contact with the first dielectric layer, the active layer comprising:

a source region;

a drain region; and a channel region situated between the source region and the drain region;

a sensing film over and in contact with the channel region;

a second dielectric layer over and in contact with the source region and the drain region;

a first electrode located within the second dielectric layer and over the drain region, the first electrode separated from the drain region by the second dielectric layer;

a second electrode located within the second dielectric layer and over the source region, the second electrode separated from the source region by the second dielectric layer; and a fluidic gate region boated over the second dielectric layer and the sensing film.

9. The device of claim 8, wherein the fluidic gate region is in contact with the sensing film.

10. The device of claim 8, wherein the second dielectric layer is in contact with a bottom surface of the first electrode and a top surface of the first electrode.

11. The device of claim 8, wherein the fluidic gate region is a cavity and the first electrode defines a portion of a perimeter of the cavity.

12. A device, comprising:

a first dielectric layer over a substrate;

an active layer over the first dielectric layer;

a source region in the active layer;

a drain region in the active layer;

a channel region in the active layer situated between the source region and the drain region;

a sensing film over the channel region, the sensing film in contact with a top surface of the source region and a top surface of the drain region;

a second dielectric layer over the active layer;

a first electrode located within the second dielectric layer; and a fluidic gate region boated over the second dielectric layer and the sensing film.

13. The device of claim 12, comprising:

a second electrode located within the second dielectric layer on a diametrically opposite side of the fluidic gate region relative to the first electrode.

14. The device of claim 13, wherein:

the first electrode is over the source region and separated from the source region by the second dielectric layer; and the second electrode is over the drain region and separated from the drain region by the second dielectric layer.

15. The device of claim 12, wherein the fluidic gate region is a cavity and the first electrode defines a portion of a perimeter of the cavity.

16. The device of claim 15, comprising:

a second electrode located within the second dielectric layer and defining a second portion of the perimeter of the cavity.

17. The device of claim 12, comprising:

a third dielectric layer over the fluidic gate region.

18. The device of claim 12, comprising:

one or more inlets coupled to the fluidic gate region.

19. The device of claim 12, comprising:

a first inlet coupled to a first fluid supply for supplying a reaction solution into the fluidic gate region; and a second inlet coupled to a second fluid supply for supplying a reset solution into the fluidic gate region.

20. The device of claim 19, comprising:

a first valve disposed between the first inlet and the fluidic gate region for controlling a supply of the reaction solution into the fluidic gate region; and a second valve disposed between the second inlet and the fluidic gate region for controlling a supply of the reset solution into the fluidic gate region.

* * * * *